(12) United States Patent
Fei

(10) Patent No.: US 9,808,399 B2
(45) Date of Patent: Nov. 7, 2017

(54) MEDICAL PHOTOTHERMAL MOXIBUSTION INSTRUMENT

(75) Inventor: Zaocheng Fei, Huzhou (CN)

(73) Assignee: Shanghai Da Rong Culture Development Co., Ltd., Shanghai (CN)

( * ) Notice: Subject to any disclaimer, the term of this patent is extended or adjusted under 35 U.S.C. 154(b) by 1071 days.

(21) Appl. No.: 13/988,340

(22) PCT Filed: Nov. 17, 2011

(86) PCT No.: PCT/CN2011/082385
§ 371 (c)(1),
(2), (4) Date: Jul. 11, 2013

(87) PCT Pub. No.: WO2012/065565
PCT Pub. Date: May 24, 2012

(65) Prior Publication Data
US 2013/0282081 A1    Oct. 24, 2013

(30) Foreign Application Priority Data
Nov. 19, 2010    (CN) .......................... 2010 1 0567201

(51) Int. Cl.
*A61B 18/06*    (2006.01)
*A61H 39/06*    (2006.01)
*A61N 5/06*    (2006.01)

(52) U.S. Cl.
CPC .......... *A61H 39/06* (2013.01); *A61N 5/0619* (2013.01); *A61H 2201/0228* (2013.01); *A61H 2201/10* (2013.01); *A61H 2201/105* (2013.01); *A61N 2005/0651* (2013.01)

(58) Field of Classification Search
CPC ........ A61H 2201/0228; A61H 2201/10; A61H 2201/105; A61H 39/06; A61N 2005/0651; A61N 5/0619; A61B 18/06; A61B 2018/064
See application file for complete search history.

*Primary Examiner* — Kami A Bosworth
*Assistant Examiner* — Deanna K Hall
(74) *Attorney, Agent, or Firm* — Kile Park Reed & Houtteman LLC

(57) ABSTRACT

A medicinal photothermal moxibustion instrument relates to a medical device. An instrument working power source and an assembly plate of a moxibustion signal adjusting system are fixed in a shell; a setting key and a medicinal photothermal moxibustion head socket are installed on an enclosure panel; and a signal connecting conductor is used to connect a plug with a moxibustion head substrate that has a medicine line slot and a light emitting diode arranged on the working face. An S-shaped medicine line slot is arranged on the working face of the moxibustion head substrate, and the medicine line slot intersects with a wire connecting two light emitting diodes on the same diameter. Then the connected plug is inserted into a moxibustion head socket and a medicine line is squeezed into the medicine line slot. The invention changes the medicine line embedding method by squeezing the medicine line into the S-shaped or reversed S-shaped curved medicine line slot, effectively solving the problems that moxibustion medicines cannot be placed in the V-shaped shallow pit of the moxibustion head and fall off easily, allowing medicinal photothermal moxibustion, and facilitating the promotion and popularization of modern moxibustion technology and the improvement of therapeutic effect.

9 Claims, 3 Drawing Sheets

MEDICAL PHOTOTHERMAL MOXIBUSTION INSTRUMENT

FIELD OF THE INVENTION

The invention relates to a medical instrument, in particular to a traditional Chinese medicine acupuncture and moxibustion apparatus.

BACKGROUND OF THE RELATED ART

Moxibustion is an important invention of the Chinese nation. Traditional moxibustion, which can treat and prevent diseases by using burning moxa to scald on acupoints, has the advantages of simple method, no side-effect, and significant effect. In order to inherit and develop the medical technology of China and promote the modernization of traditional acupuncture and moxibustion the moxibustion has been technically improved by utilizing modern electroheat control technology to replace and regulate the moxibustion, and also realized the functions of reinforcing and reducing in terms of control technology. Such technical measures have certain effects on the development of traditional acupuncture and moxibustion technology. However, the disadvantages are that: heat and light effects of burning moxa are mainly taken into consideration when burning moxa is replaced with electroheat technology for moxibustion in modern moxibustion, injecting heat and light energy to the acupoint. In the thousands of years of development of traditional moxibustion, it has been concluded corresponding medicines must be combined for moxibustion against (referred to as medicinal moxibustion). On this basis, the medicines can be scientifically utilized to achieve better treatment effects. There is still a lack of corresponding measures on how to utilize different wave lengths in the technical improvement of modern moxibustion. Although the technology of arranging a shallow pit for embedding a medicinal cake (tablet) on the surface of a moxibustion head and placing the medicinal cake into the shallow pit for moxibustion has been developed for medicinal moxibustion, placement of the medicinal cake on the working face of the head will certainly increase resistances and barrier to the release and transfer of moxibustion heat and light energy as the medicinal cake has a certain area and thickness, affecting the moxibustion effect. What is worse, the medicinal cake can not be placed in the shallow pit on the surface of the moxibustion head and falls off easily as the pit is very shallow, thus the operation is troublesome and difficult. Therefore, "medicinal moxibustion" in the modern moxibustion is not available and not used for a long time.

SUMMARY OF THE INVENTION

The purpose of the invention is to inherit the essence of traditional moxibustion technology completely to solve the disadvantages in the related art. The invention can effectively prevent the moxibustion tablet from falling off from the shallow pit of the moxibustion head through firmly placing the moxibustion medicine. In addition, the invention has a plurality of medicinal photothermal moxibustion structure based on different sensitivities of different visceral diseases to heat, light and medicines for moxibustion, so as to meet the demands of medicinal photothermal moxibustion, medicinal optical moxibustion and medicinal thermal moxibustion technologies, so that a doctor can conveniently select a plurality of medical moxibustion technologies, and the medicinal moxibustion technology of the traditional moxibustion can be inherited and improved in a better manner.

A technical solution for solving the technical problem in the invention is to design a shell internally fixed with an instrument working power source, and a control system assembly plate of an electronic photothermal moxibustion signal adjusting system. A power switch, a setting key and a plurality of moxibustion head sockets are installed on an enclosure panel. A photothermal moxibustion signal connecting conductor is used to connect a plug with a moxibustion head of a moxibustion head substrate that is plastically packaged and has a heating element and a light emitting diode installed inside. The connected plug is inserted into the moxibustion head socket. A medicine line slot and two light emitting diodes are arranged on the working face of the moxibustion head substrate. The medicine line slot intersects with a wire connecting the two light emitting diodes. A medicine line is squeezed into the medicine line slot and the moxibustion head is placed into a therapeutic acupoint on the surface of a body. When the control system sends out a thermal moxibustion signal, medicine properties in the medicine line will be slowly evaporated to the acupoint on the surface of the body as the temperature rises, capillaries beneath the skin at the acupoint will further dilate as the temperature rises slowly, and then the medicine properties can penetrate into the skin more smoothly under heat, and have good synergistic effect with heat and light energy in moxibustion to trigger the acupoint and stimulate meridians and collaterals so as to achieve an ideal moxibustion effect.

In order to meet the demands of selecting a plurality of medicinal photothermal moxibustion technologies such as medicinal optical moxibustion, medicinal optical moxibustion and medicinal thermal moxibustion, said working face of the moxibustion head substrate has three structures. The structure of the working face of a medicinal photothermal moxibustion substrate is that a light emitting diode and a medicine line slot are arranged on the working face of the moxibustion head substrate and a heating element is installed in the moxibustion head substrate; the structure of the working face of a medicinal optical moxibustion substrate is that two light emitting diodes and a medicine line slot are installed on the working face of the moxibustion head substrate, and a heating element is not installed inside the moxibustion head substrate; and the structure of the working face of a medicinal thermal moxibustion substrate is that only two colored circle imprints higher than the working face of the moxibustion head substrate by no more than 5 mm and a medicine line slot are arranged at the position of the original circular light emitting diode mounting hole on the working face of the moxibustion head substrate instead of a light emitting diode, and a resistance heating element is arranged in the moxibustion head substrate.

Four peripheries of said working face of the moxibustion head substrate take the shape of a circle, an ellipse or a polygon. The out-of-roundness of a circular working face of the moxibustion head substrate is less than two fifths of the nominal diameter, and the radius difference at two ends of an elliptic working face of the moxibustion head substrate is less than two thirds of the radius at the larger end.

A medicine line slot on the same diameter of said circular working face of the moxibustion head substrate can be an S-shaped or reversed S-shaped semi-circular arc with a radius of curvature between one fifth and three fourths of the diameter of the working face of the moxibustion head substrate; the circle center of the medicine line slot is respectively overlapped with installation centers of the two light emitting diodes, and the overlapping error is less than one fifth of the diameter of the working face of the moxibustion head substrate. The central point of said circular working face of the moxibustion head substrate, the central point of the medicine line slot and the central point of the wire connecting the two light emitting diodes are overlapped, and the overlapping error is less than one fifth of the diameter of the working face of the moxibustion head substrate.

The light emitting diodes on said circular working face of the moxibustion head substrate are symmetrically distributed and installed on the same diameter of the working face of the moxibustion head substrate. The distance between the two light emitting diodes is more than one fourth of the diameter of the working face of the moxibustion head substrate, and the location error of installation points of the two light emitting diodes is less than one fifth of the working face of the moxibustion head substrate.

The medicine line slot on said circular working face of the moxibustion head substrate is 0-5.0 mm deep and 0.1-5.0 mm wide. A pigment coating is coated at the bottom of the slot. Two coatings of different colors are coated on the working faces at two sides of the medicine line slot.

In order to meet the demands of using different wavelengths in red, orange, yellow, green, cyan, blue and purple for effective moxibustion therapy of different diseases and different viscera, said light emitting diodes can use semiconductor light emitting diodes and semiconductor laser diodes with single color of red, orange, yellow, green, cyan, blue or purple or use color-adjustable semiconductor light emitting diodes with multiple colors of red, orange, yellow, green, cyan, blue and purple adjustable by working current.

Said medicine line squeezed in the medicine line slot can be a noodle-shaped 1-5 mm thick medicine line prepared and twisted by adding a blender to a special concentrated herbal extract for moxibustion, or a medicine line made by dipping a cotton yarn with a diameter of 1-5 mm into the special concentrated herbal extract for moxibustion.

Beneficial Effects of the Invention

1. As it is very convenient to embed the medicine line and clear the medicine line, the invention is more acceptable to doctors, thus facilitating the promotion and popularization of medicinal photothermal moxibustion technology, and the improvement of modern moxibustion effect.

2. As friction exists at two sides inside the medicine line slot, and the medicine line slot has a certain curvature, the medicine line does not fall off easily after being squeezed in the medicine line slot, solving the problem of difficulty in placing the medicinal cake, and overcoming the impact of barriers to heat and light energy transfer on moxibustion effects due to medicinal cake.

3. The invention meets the requirements for selection of different medicinal moxibustion therapies for different diseases during moxibustion allowing further development of the traditional moxibustion.

BRIEF DESCRIPTIONS OF THE DRAWINGS

The invention will be further described in combination with accompanying drawings and embodiments.

Figure 1:
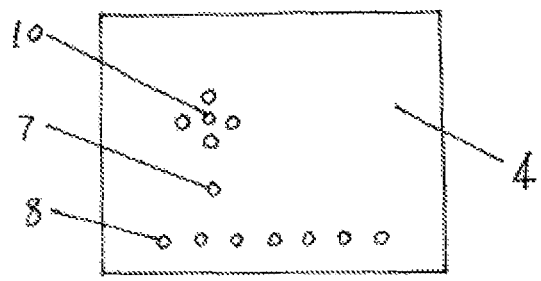
FIG. 1 is layout of an instrument control panel of the embodiment.

In the drawings: 1—color-adjsutable LED (light emitting diode), 2—electric heating element, 3—working face of moxibustion head substrate, 4—enclosure panel electronic medicinal photothermal moxibustion signal adjusting system, 6—instrument working power source, 7—power switch, 8—moxibustion head socket, 9—moxibustion head, 10—setting key, 11—color-adjsutable LED mounting hole, 12 medicine line slot, 13 assembly plate, 14—shell, 15—connecting conductor, and 16—moxibustion head substrate.

DESCRIPTIONS OF THE PREFERRED EMBODIMENTS

Figure 2:
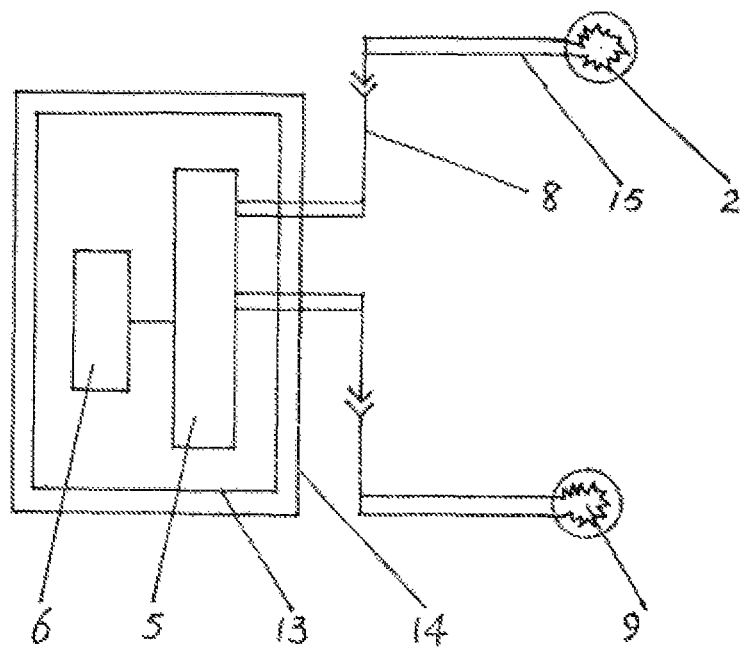
FIG. 2 is a schematic diagram of an instrument of the embodiment.
Figure 3:
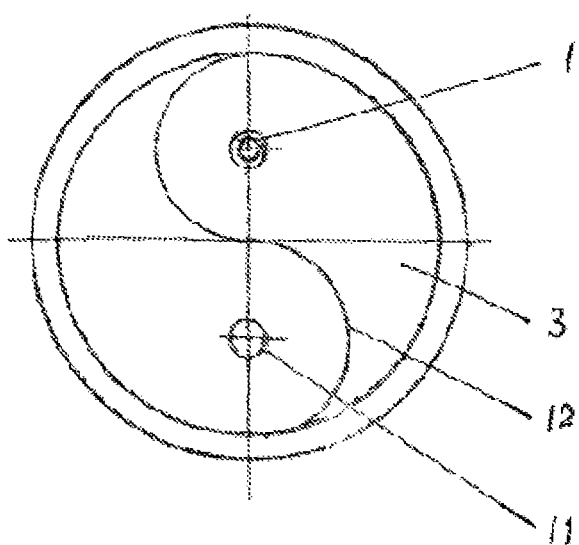
FIG. 3 is a front view of the working face of a medicinal photothermal moxibustion head substrate of the embodiment.
Figure 4:
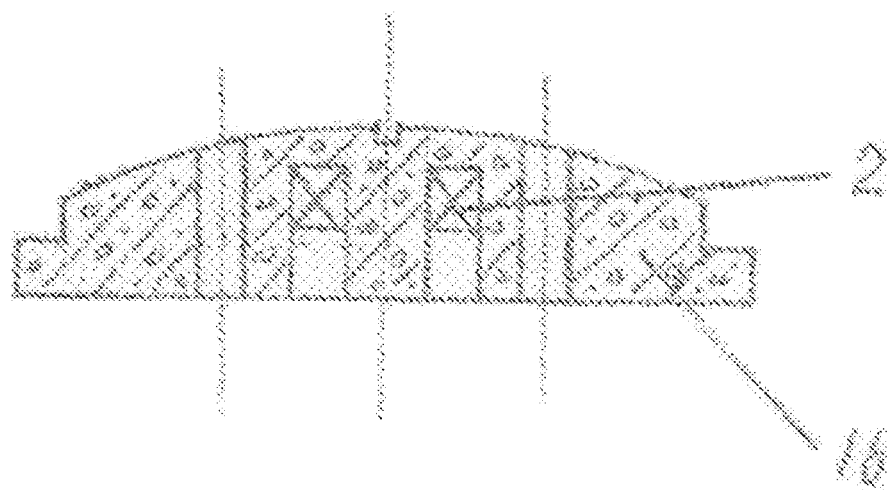
FIG. 4 is a sectional view of the medicinal photothermal moxibustion head substrate of the embodiment.

In the embodiments as shown in FIG. 1, FIG. 2, FIG. 3 and FIG. 4, a shell (14) internally fixed with an instrument working power source (6), and a control system assembly plate (13) of an electronic photothermal moxibustion signal adjusting system (5) is designed. A power switch (7), a setting key (10) and a plurality of moxibustion head sockets (8) are installed on an enclosure panel (4). A photothermal moxibustion signal connecting conductor (15) is used to connect a plug with a moxibustion head (9) that is plastically packaged, has a medicine line slot (12) arranged on the working face (3) of the moxibustion head substrate, has a color-adjustable LED (1) with a diameter of 3 mm installed in a color-adjustable LED mounting hole (11), and has a heating element (2) with resistance of 60Q installed in a moxibustion head substrate (16). Then the connected plug is inserted into the moxibustion head socket (8), and a medicine line is squeezed in the medicine line slot (12).

The out-of-roundness of the circular working face (3) of the moxibustion head substrate is less than 1.2 mm. The center of the medicine line slot (12) curved as an S shape and arranged on the working face (3) of the moxibustion head interacts with the center of the wire connecting the two LEDs (1) with a diameter of 3 mm and colors of red, orange and yellow adjustable by changing the working current.

The two circle centers of two semi-circular arcs with a radius of 8 mm at two ends of the medicine line slot (12) are respectively overlapped with the installation centers of the two color-adjustable LEDs (1), and the overlapping error is less than 1 mm.

The two color-adjustable LEDs (1) are symmetrically installed on the same diameter of the working face (3) of the moxibustion head substrate with a diameter of 32 mm, and the location error of installation points of the two color-adjustable LEDs (1) is less than 1 mm.

The central point of the wire connecting the circle centers of the two semi-circular arcs at the two ends of the medicine line slot (12), the central point of the wire connecting the two color-adjustable LEDs (1), and the central point of the working face (3) of the moxibustion head substrate are overlapped; and the overlapping error is less than 1.5 mm. The medicine line slot (12) is 1.8 mm deep and 2 mm wide. A yellow pigment coating is coated at the bottom of the slot, and black and white environment-friendly coatings are coated on the working faces at the two sides of the medicine line slot.

The structure of the working face of the medicinal optical moxibustion head substrate that emits light only and does not gives out heat is as follows: two color-adjustable LEDs (1) and a medicine line slot (12) are arranged on the working face (3) of the moxibustion head substrate, and a heating element (2) is not installed in the moxibustion head substrate.

The structure of the working face of the medicinal thermal moxibustion head substrate that does not emit light and gives out heat only is as follows: only two red-and-yellow circle imprints with a diameter of 3 mm and 1.5 mm higher than the working face of the moxibustion head substrate and a medicine line slot (12) are arranged at the position of the original circular light emitting diode mounting hole on the working face (3) of the moxibustion head substrate instead of a light emitting diode, and a heating element (2) with resistance of 60Q is installed in the moxibustion head substrate.

The medicine line squeezed in the medicine line slot (12) is a noodle-shaped medicine line prepared and twisted by adding fine calcium carbonate powder with a fineness of 300 meshes to a special concentrated herbal extract for moxibustion.

When in use, the instrument is plugged in and then the power switch (7) is switched on. A moxibustion signal is set through the setting key (10), and wavelength of required color (e.g., red) for the disease (e.g., heart disease) to be treated is modulated, and then the medicinal photothermal moxibustion head (9) filled with a medicine line is bound to an acupoint (e.g., Neiguan Point) subject to moxibustion for medicinal photothermal moxibustion of a patient with heart disease.

After the treatment, the power is cut off, the medicinal photothermal moxibustion head (9) is taken off, and the medicine line in the medicine line slot (12) is cleared.

What is claimed is:

1. A medicinal photothermal moxibustion instrument, comprising:
   a shell internally fixed with an instrument working power source;
   an electronic photothermal moxibustion signal adjusting system including a control system assembly plate, wherein the control system assembly plate includes a power switch, a setting key and a plurality of moxibustion head sockets being installed on an enclosure panel of the control system assembly plate;
   a photothermal moxibustion signal connecting conductor connecting a plug with a moxibustion head of a moxibustion head substrate that is plastically packaged;
   a heating element and/or a light emitting diode installed inside the moxibustion head substrate; wherein the plug is inserted into the moxibustion head socket, and a medicine line is squeezed into a medicine line slot arranged on a working face of the moxibustion head substrate, and the medicine line slot intersects with a wire connecting two light emitting diodes.

2. The medicinal photothermal moxibustion instrument according to claim 1, wherein the working face of the moxibustion head substrate is of a shape of a circle, an ellipse or a polygon, wherein an out-of-roundness of a circular working face of a circular-shaped moxibustion head substrate is less than two fifths of a nominal diameter of the circular-shaped moxibustion head substrate, and a shortest radius of an elliptic working face of an elliptical-shaped moxibustion head substrate is less than two thirds of a longest radius of the elliptic working face of the elliptical-shaped moxibustion head substrate.

3. The medicinal photothermal moxibustion instrument according to claim 2, wherein the medicine line slot arranged on the circular working face of the circular-shaped moxibustion head substrate is of an S-shaped formed by two circular-shaped arc with a radius of curvature ranged between one fifth and three fourths of a diameter of the circular working face of the circular-shaped moxibustion head substrate, a center of the medicine line slot is overlapped with a center of the two light emitting diodes, and an overlapping offset-is less than one fifth of the diameter of the circular working face of the circular-shaped moxibustion head substrate.

4. The medicinal photothermal moxibustion instrument according to claim 2, wherein a central point of the circular working face of the circular-shaped moxibustion head substrate, a central point of the medicine line slot and a central point of the wire connecting the two light emitting diodes are overlapped; and an overlapping offset is less than one fifth of the diameter of the circular working face of the circular-shaped moxibustion head substrate.

5. The medicinal photothermal moxibustion instrument according to claim 2, wherein the two light emitting diodes on the circular working face of the circular-shaped moxibustion head substrate are symmetrically distributed and installed on a same diameter of the circular working face of the circular-shaped moxibustion head substrate; a distance between the two light emitting diodes is more than one fourth of the diameter of the circular working face of the circular-shaped moxibustion head substrate.

6. The medicinal photothermal moxibustion instrument according to claim 1, wherein the moxibustion head substrate is selected from one of the following three configurations, including:
   the two light emitting diodes and the medicine line slot being arranged on the working face of the moxibustion head substrate, and the heating element being installed inside the moxibustion head substrate;
   the two light emitting diodes and the medicine line slot being installed on the working face of the moxibustion head substrate, without heating element being installed inside the moxibustion head substrate; and
   two colored circle imprints being arranged at two mounting holes of the two light emitting diodes with the two light emitting diodes not being installed on the two mounting holes and the two colored circle imprints being higher than the working face of the moxibustion head substrate by no more than 5 mm, and the heating element being arranged in the moxibustion head substrate.

7. The medicinal photothermal moxibustion instrument according to claim 1, wherein the medicine line slot on the working face of the moxibustion head substrate is 0-5.0-mm deep and 0.1-5.0-mm wide, the medicine line slot divides the working face into two portions, a pigment coating is coated at the bottom of the medicine line slot, and two coatings of different colors are respectively coated on surfaces of the two portions of the working faces divided by the medicine line slot.

8. The medicinal photothermal moxibustion instrument according to claim 1, wherein the two light emitting diodes on the working face of the moxibustion head substrate are semiconductor light emitting diodes and semiconductor laser diodes with single color of red, orange, yellow, green, cyan, blue or purple, or use color-adjustable semiconductor light emitting diodes with multiple colors of red, orange, yellow, green, cyan, blue and purple.

9. The medicinal photothermal moxibustion instrument according to claim 1, wherein the medicine line squeezed in the medicine line slot is a noodle-shaped 1-5 mm thick medicine line prepared and twisted by adding a blender into a special concentrated herbal extract for moxibustion, or a medicine line made by dipping a cotton yarn with a diameter of 1-5 mm into the special concentrated herbal extract for moxibustion.

* * * * *